(12) United States Patent
Ringvad Andersen et al.

(10) Patent No.: US 9,861,794 B2
(45) Date of Patent: Jan. 9, 2018

(54) MULTI CHAMBER MEDICAL BALLOON

(71) Applicant: COOK MEDICAL TECHNOLGOES LLC, Bloomington, IN (US)

(72) Inventors: Bo Ringvad Andersen, Koege (DK); Kim Holm Andersen, Ringsted (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 15/288,157

(22) Filed: Oct. 7, 2016

(65) Prior Publication Data

US 2017/0100568 A1    Apr. 13, 2017

(30) Foreign Application Priority Data

Oct. 8, 2015  (GB) .................................. 1517831.2

(51) Int. Cl.
| | |
|---|---|
| *A61L 29/02* | (2006.01) |
| *A61M 25/10* | (2013.01) |
| *A61L 29/06* | (2006.01) |
| *A61L 29/18* | (2006.01) |

(52) U.S. Cl.
CPC ............. *A61M 25/10* (2013.01); *A61L 29/02* (2013.01); *A61L 29/06* (2013.01); *A61L 29/18* (2013.01); *A61L 2400/00* (2013.01); *A61M 2025/1059* (2013.01); *A61M 2025/1072* (2013.01); *A61M 2025/1075* (2013.01); *A61M 2025/1079* (2013.01)

(58) Field of Classification Search
CPC .......... A61M 25/10; A61M 2025/1059; A61M 2025/1072; A61M 2025/1075; A61M 2025/1079; A61L 29/02; A61L 29/06; A61L 29/18; A61L 2400/00
See application file for complete search history.

(56) References Cited

U.S. PATENT DOCUMENTS

| | | |
|---|---|---|
| 5,304,135 A | 4/1994 | Shonk |
| 5,501,667 A | 3/1996 | Verduin, Jr. |
| 5,599,306 A | 2/1997 | Klein et al. |

(Continued)

FOREIGN PATENT DOCUMENTS

| | | |
|---|---|---|
| WO | WO 03/059213 A2 | 7/2003 |
| WO | WO 2006/037608 A1 | 4/2006 |

OTHER PUBLICATIONS

GB1517831.2, Examination Report, dated Dec. 12, 2016.

(Continued)

*Primary Examiner* — Michael C Miggins
(74) *Attorney, Agent, or Firm* — Brinks Gilson & Lione

(57) ABSTRACT

A medical balloon includes at least one internal wall dividing the balloon into a plurality of separate chambers which may be separately inflatable and deflatable. The at least one internal wall is impregnated with heat conductive particles. The heat conductive particles enable heat produced during the balloon blowing process to pass through the polymer material of the balloon and specifically into the internal wall or walls, enabling these to soften and stretch during the process. This improves the integrity of the balloon and also balloon flexibility. The radiopaque particles embedded in the internal wall or walls of the balloon can also, in preferred embodiments, be of radiopaque material, providing the balloon with imaging visibility during deployment thereof in a patient.

20 Claims, 5 Drawing Sheets

(56) References Cited

U.S. PATENT DOCUMENTS

| | | |
|---|---|---|
| 8,523,842 B2 | 9/2013 | Iguchi |
| 2003/0032963 A1 | 2/2003 | Reiss et al. |
| 2007/0010845 A1 | 1/2007 | Gong et al. |
| 2009/0299327 A1 | 12/2009 | Tilson et al. |
| 2010/0010470 A1 | 1/2010 | Bates |
| 2012/0089220 A1 | 4/2012 | Lualdi |
| 2013/0123832 A1 | 5/2013 | Weber et al. |
| 2015/0066069 A1 | 3/2015 | Drasler et al. |
| 2015/0094657 A1 | 4/2015 | Byrne et al. |

OTHER PUBLICATIONS

European Extended Search Report for EP 16275149.9-1501, dated Mar. 7, 2017.
GB1517831.2, Combined Search and Examination Report, dated Mar. 9, 2016.
Examination Report for GB1517831.2 dated Aug. 17, 2017.

MULTI CHAMBER MEDICAL BALLOON

CROSS-REFERENCE TO RELATED APPLICATIONS

This application claims the benefit of priority under 35 U.S.C. §119(a) to Great Britain Patent Application No. GB 1517831.2, filed Oct. 8, 2015, which is hereby incorporated by reference in its entirety.

TECHNICAL FIELD

The present invention relates to a medical balloon for use in a variety of medical treatments including, for example, for angioplasty procedures, medical device implantation, valvuloplasty, rehabilitation of airways, temporary vessel occlusion, and so on.

BACKGROUND ART

Medical balloons are well known in the art. A conventional balloon assembly includes an expandable balloon fitted at the distal end of a carrier catheter, the catheter having at least one lumen fluidically connected to the internal volume of the balloon and arranged to supply fluid to expand, or inflate, the balloon, and to exhaust fluid from the balloon so as to collapse the balloon at the end of the medical procedure. Medical balloons of this nature are generally circular in transverse cross-section and have their two ends fixed in fluid tight manner to the balloon catheter such that the internal volume, or chamber, of the balloon is sealed to the environment. Whilst it is relatively simple to form a balloon which has a varying diameter along its length, it is harder to alter the cross-sectional shape of the balloon as the inflation pressure causes the balloon wall to tend to a circle. Attempts to make a balloon with cross-sectional shapes other than round when inflated have met with practical difficulties, including increased stiffness of the balloon particularly when deflated, increased tendency to rupture, poor repeatability and stability of the inflated shape, and so on.

Examples of medical balloons and catheters having a plurality of chambers of non-round cross-sections can be found in US 2007/0010845, U.S. Pat. No. 5,501,667, US 2015/0094657, U.S. Pat. No. 5,304,135, US 2003/0032963 and WO 2006/037608.

SUMMARY OF THE PRESENT INVENTION

The present invention seeks to provide an improved medical balloon and specifically a multi-chamber medical balloon.

According to an aspect of the present invention, there is provided a medical balloon assembly including a balloon having a body portion, the body portion being formed of a balloon wall providing an expandable volume within the balloon, the expandable volume being divided into a plurality of chambers by a least one internal wall extending between opposing sides of the balloon wall, the balloon wall and internal wall being formed from a flexible polymer material, the polymer material of the internal wall having heat conductive particles embedded therein.

The heat conductive particles in the internal wall have the function of transferring heat during the balloon blowing process into the internal walls, allowing these to soften and expand, with the result that the balloon can be properly formed. This can also optimise the flexibility of the formed balloon, even though the balloon includes additional walls compared to a standard cylindrical single chamber balloon. The provision of a balloon with internal walls can also provide a balloon with multiple chambers, permitting the formation of a balloon with a non-round axial shape and also or in the alternative a balloon which can be selectively inflated.

The heat conductive particles have a thermal conductivity which is greater than the thermal conductivity of the material of the internal wall. In embodiments, the thermal conductivity of the heat conductive particles is at least 50 times greater than the thermal conductivity of the material of the internal wall. In some embodiments, the thermal conductivity of the heat conductive particles is at least 100, or at least 200, times greater than the thermal conductivity of the material of the internal wall. Preferably, the thermal conductivity of the heat conductive particles is at least 500 times greater than the thermal conductivity of the material of the internal wall.

In some embodiments, the thermal conductivity of the heat conductive particles is at least 20 W/(mK), at least 60 W/(mK), or preferably at least 150 W/(mK).

Advantageously, the balloon wall has exterior and interior surfaces and a wall thickness between the exterior and interior surfaces, the internal wall extending to the interior surface of the balloon body portion. In other words, the internal wall preferably does not extend to the outer surface of the balloon, enabling the balloon wall material to act as a barrier to the heat conductive particles relative to surrounding body tissue.

Preferably, the balloon body portion is substantially free of the heat conductive particles of the internal wall. In the preferred embodiments, the balloon wall is made of polymer material only.

The balloon wall may be made of a single layer of material or of multiple layers of material. The internal wall is preferably made of a single layer of material, and may be uniform in consistency throughout its volume.

The heat conductive particles may be of or include a metal or metal alloy. They may also be made of or include a radiopaque material.

In the preferred embodiment, the heat conductive particles are or include tungsten. Tungsten is a preferred material as it exhibits good heat conductive properties and is also radiopaque, which results in the balloon being visible to imaging during the deployment of the balloon in a patient.

In other embodiments, the heat conductive particles are or include at least one of: boron, gold, silver, platinum, palladium and copper.

Advantageously, the internal wall includes around or at least 50% by weight of heat conductive particles.

The density of heat conductive particles in the internal wall may be around 2 g/cc, in one example 1.92 g/cc, and the specific volume around 0.5 g/cc, in one example 0.521 g/cc.

Preferably, the heat conductive particles have an average particle size of less than one to tens of micrometres, in one embodiment in the region of 0.50 to 1.0 micrometres. They may have a substantially round or elongate shape, advantageously a rounded oblong shape. It has been found that such shape and size provide optimum characteristics in terms of conducting heat to the internal wall or walls during formation of the balloon from a raw tubing.

The heat conductive particles are preferably substantially evenly distributed throughout the internal wall or walls, although in other embodiments they may have a differing distribution, for instance to have a greater concentration or density further away from the external surfaces of the balloon or raw tubing.

In the preferred embodiments, the balloon wall and the internal wall or walls are made from the same polymer material. In some embodiments, the balloon wall and the at least one internal wall are made from a polyamide, for example of nylon, preferably nylon 12.

The balloon may include a plurality of internal walls. The or at least two of said internal walls may be disposed substantially parallel to one another. In addition or in the alternative, they may be disposed to cross one another.

The body portion may be generally circular or non-circular in transverse cross-section. It may, for instance, be generally oval in transverse cross-section.

In some embodiments, the internal wall generates an external channel or depression in an exterior surface of the balloon on inflation of the balloon. This can be very useful in some medical applications, for instance where the balloon may be positioned adjacent an organ requiring protection from the pressure generated by the balloon. An example are the vocal cords for a balloon intended to treat the trachea.

The at least one internal wall advantageously divides the balloon into fluidically separate chambers.

Other features and advantageous of the invention taught herein will be apparent from the following description and accompanying drawings.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
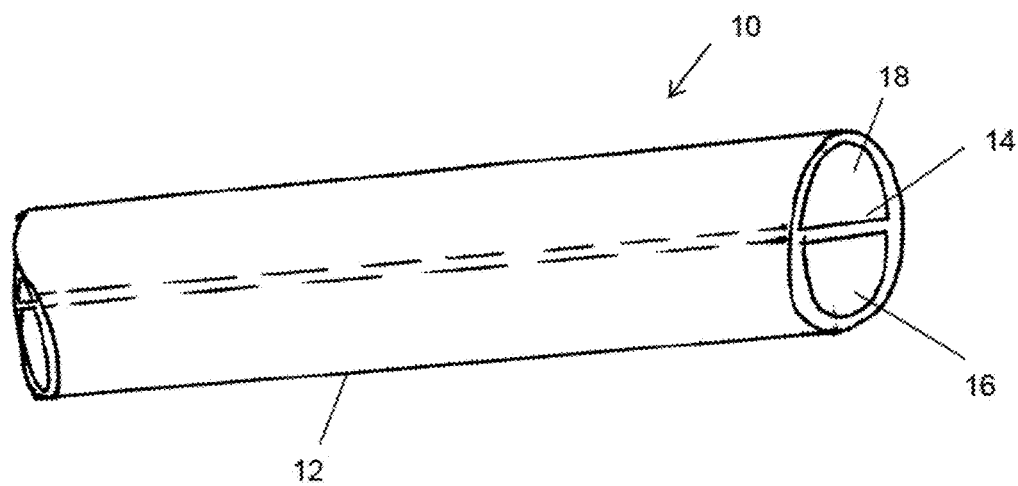
FIG. 1 is a schematic perspective view of an embodiment of raw tubing for forming a medical balloon according to the teachings herein.

Described below are various embodiments of medical balloon and balloon catheter assembly according to the teachings herein. The skilled person will appreciate that only some embodiments are described and that a medical balloon having additional features and characteristics over and above the described embodiments will be readily understandable to the person skilled in the art, such as having more chambers, different balloon shapes and so on.

The drawings shown are schematic and not to scale, and they depict only the major components of the device taught herein. The skilled person will be familiar with the typical characteristics in terms of dimensions and proportions of the various components.

In the described embodiments, the balloon is preferably formed from a raw tubing, typically made of a polymer material, which is inflated under pressure and at heat in order to cause the raw tubing to expand within a mold and to form a balloon shape. This is a technique which is well-known in the art.

A medical balloon is typically formed as a cylindrical structure having a body portion and at either end conical end portions. The end portions extend to necks which are bonded in fluid tight manner to a distal end of a carrier catheter. Generally, though not necessarily, the balloon wall is impermeable and forms a fluid tight chamber over the carrier catheter. The carrier catheter typically has one or more lumens extending through the length of the catheter, with at least one of these lumens having a port fluidically coupled to the internal chamber of the balloon. Fluid, typically saline liquid, can be fed into the balloon through the lumen in the carrier catheter so as to inflate, or expand, the balloon to its operating condition. Expansion fluid can also be exhausted through the lumen, so as to cause the balloon to collapse and preferably to wrap around the carrier catheter in order to permit easy withdrawal of the medical balloon from within vessel or other organ of a patient.

The wall of the balloon is preferably as thin as possible, in order to optimise the flexibility of the balloon and also reduce the footprint, that is the diameter, of the deflated balloon for endoluminal deployment.

As a result of the inflation pressures used, the balloon will typically expand to the most efficient shape, specifically round in axial cross-section, although it is known to have balloons having different diameters along its length in order to generate a profiled shape, such as an hourglass or tapering profile.

It is also known to have balloons with multiple layers, for instance for drug elution and for other purposes. The teachings herein apply also to such multi-layered balloon structures.

As it will become apparent from the description of the specific embodiments below, the teachings herein provide a balloon structure which is divided into a plurality of chambers by at least one internal wall extending between opposing sides of the balloon wall. Such an internal wall can divide the expandable volume of the balloon into a plurality of separate chambers, which in the preferred embodiments can be individually filled with or exhausted of inflation fluid, such that the balloon can be differentially inflated in dependence upon the medical procedure.

It is also important for the balloon to retain its structure during normal and expected operating conditions, without the balloon rupturing or losing its intended shape during the medical procedure. Whilst attempts have been made to form internal structures or partitions within a balloon for this purpose, the inventors have discovered that any internal device of this nature can compromise the integrity of the balloon and can result in loss of flexibility of the balloon, making known structures unsuitable for many medical applications.

Referring now to FIG. 1, this shows in schematic form a perspective view of a simple embodiment of raw tubing 10 for use in the manufacture of a medical balloon. In the example shown in FIG. 1, the raw tubing 10 includes a major portion 12 of generally cylindrical form and an internal wall 14 which extends throughout the length of the major portion 12 and is attached to or otherwise integral with opposing sides of the major portion 12. The internal wall 14 divides the raw tubing into first and second chambers 16, 18 which are, in the preferred embodiment, fluidically separate from one another.

Typically, the raw tubing 10 will have a diameter which is consistent with that of the catheter upon which the balloon is to be fitted, such that the raw tubing 10 substantially at its original diameter can create the necks of the balloon.

The raw tubing 10 need not have a circular cylindrical shape and in many embodiments may have a different shape. Generally, the shape of the raw tubing will be related to the final desired shape of the balloon.

Figure 2:
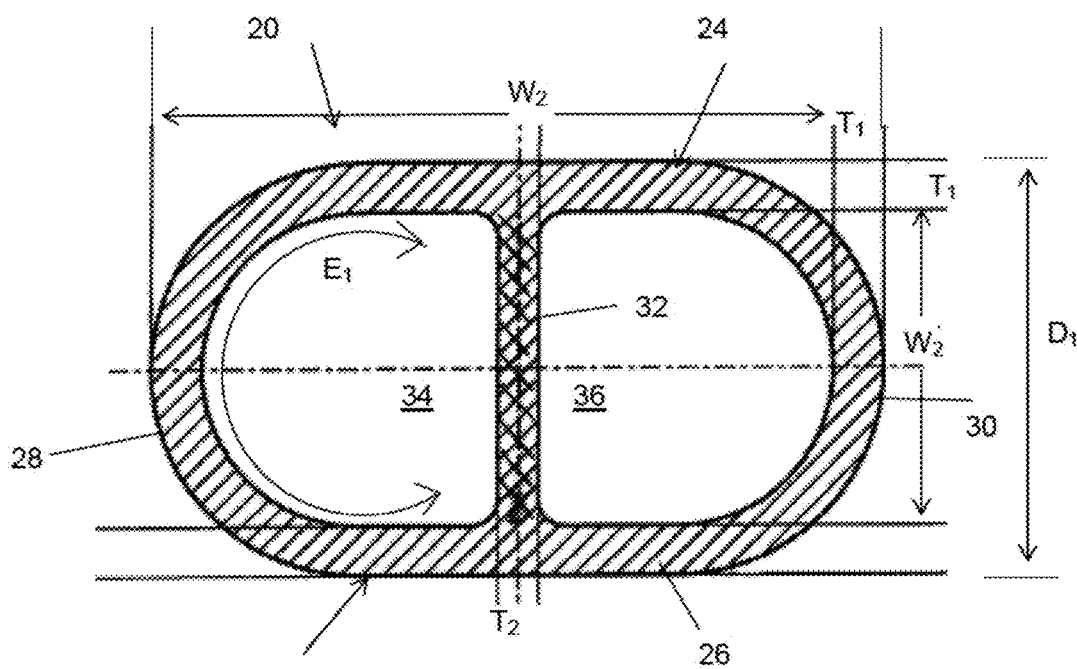
FIG. 2 is a transverse cross-sectional view of an embodiment of raw tubing according to the teachings herein.

Referring now to FIG. 2, this shows a transverse cross-sectional view of raw tubing similar to that of FIG. 1. The raw tubing 20 of FIG. 2 has a cylindrical outer wall 22 which in this embodiment is shown as being generally oval, having first and second opposing sides 24, 26 joined to one another by rounded sections 28, 30 and by an internal wall 32 described in further detail below.

In the example shown in FIG. 2, the raw tubing 20 has a first depth $D_1$ and a width $W_2$, the width $W_2$ being greater than the depth $D_1$. The balloon wall 22 has, in this example, a uniform wall thickness $T_1$, although in other embodiments the balloon wall may have varying thicknesses across its extent. The balloon wall 22 can be made of any suitable material, typically a polymer material. A preferred material is a polyamide, preferably nylon 12. Other materials include a medical grade polyurethane, PET or other polyester elastomer. An example is Hytrel®.

Integral with the opposing sides 24, 26 is the internal wall 32, which extends throughout the length of the raw tubing 20, in a manner similar to the example shown in FIG. 1. The internal wall 32, in this embodiment, divides the balloon wall 22 into two equal components, so as to create two separate lumens or chambers 34, 36 of the same or similar dimensions.

The internal wall 32 has a width $W_2$ which is smaller than the depth $D_1$ of the cylindrical portion 22, the difference being twice the thickness of the balloon wall 22, that is twice $T_1$. The width $W_2$ of the internal wall 32, relative to the extent of the balloon wall extending from one end of the internal wall 32 to the other, shown as $E_1$ in FIG. 2, will in practice determine the amount by which each half of the cylindrical portion 22 will inflate beyond the width $W_2$ of the internal wall 32 upon inflation of the chambers 34, 36 and, as a result, the eventual shape of the balloon. This is explained in further detail below. In practice, a larger dimension $E_1$ will cause greater deviation beyond $W_2$ (and in practice $D_1$) than when $E_1$ is smaller.

Figure 3:
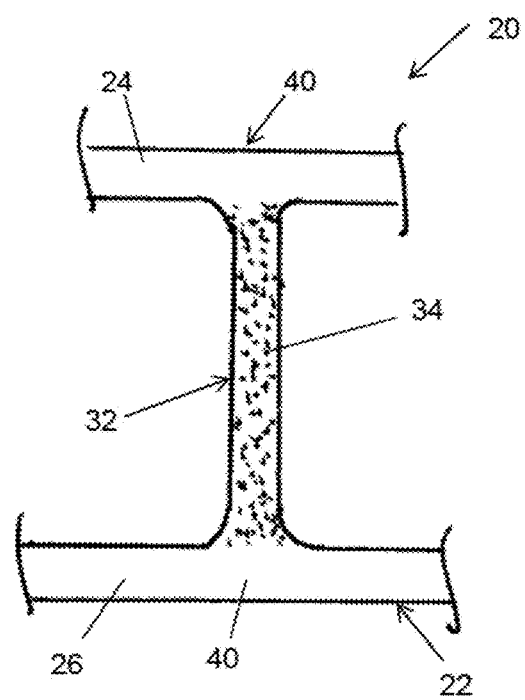
FIG. 3 shows in enlarged form a part of the raw tubing of FIG. 2.

With reference now to FIG. 3, its shows a cutaway section of the raw tubing 20. The internal wall 32 is preferably made of a polymer material, advantageously but not necessarily the same material as that of the wall 22 of the raw tubing 20. Within the material forming the internal wall 32 there is embedded a mass of heat conductive particles 34, for the purposes described in further detail below. The heat conductive particles may be of metal or metal alloy and in the preferred embodiment are also of a radiopaque material. Examples include boron, gold, silver, platinum, palladium, copper, or other known radiopaque materials. The preferred material is tungsten, which the inventors have discovered has optimal heat conductive properties for this application and also good radiopacity.

The heat conductive particles have a thermal conductivity which is greater than the thermal conductivity of the material of the internal wall. In embodiments, the thermal conductivity of the heat conductive particles is at least 50 times greater than the thermal conductivity of the material of the internal wall. In some embodiments, the thermal conductivity of the heat conductive particles is at least 100, or at least 200, times greater than the thermal conductivity of the material of the internal wall. Preferably, the thermal conductivity of the heat conductive particles is at least 500 times greater than the thermal conductivity of the material of the internal wall.

In some embodiments, the thermal conductivity of the heat conductive particles is at least 20 W/(mK), at least 60 W/(mK), or preferably at least 150 W/(mK).

The internal wall 32 may have around 50% by weight of heat conductive particles, although other embodiments may have substantially more than 50% by weight. The concentration of heat conductive particles should be balanced between providing optimal conduction of heat without resulting in degradation of the structural integrity of the internal wall 32, loss of flexibility and loss of ability to stretch during inflation of the raw tubing in order to form the medical balloon. In a practical embodiment using nylon for the polymer material and tungsten for the particles, the proportion of heat conductive particles within the internal wall was in the region of 52%.

The heat conductive particles preferably have a density in the region of 2 grams/cm$^3$, in the practical embodiment indicated above a density of around 1.92 grams/cm$^3$. The specific volume of the formulation may be in the region of 0.50 grams/cm$^3$, in the specific example 0.521 grams/cm$^3$. The heat conductive particles may have an average particle size of 0.50 to 2.0 micrometres. They preferably have an average particle size of between 0.50 and 0.99 micrometres, although in other embodiments may have an average particle size of from less than a micrometre to tens of micrometres, for instance up to 10 to 25 micrometres.

The heat conductive particles may be of a rounded or generally spherical shape, although it is preferred that they have an elongate shape. They could, for instance, be a very rounded oval shape which could be described as being somewhat like the shape of an asteroid.

The heat conductive particles are preferably even distributed throughout the material of the inner wall 32, although in other embodiments their distribution may vary through the internal wall 32. Varying the concentration of heat conductive particles can alter the heat transfer characteristics through the internal wall as will be apparent from the teachings below.

It is preferred that the heat conductive particles 34 are kept within the volume of the internal wall 32, that is they do not extend into the wall 22 of the raw tubing 20. Thus, and as will be apparent in particular from FIG. 3, it is preferred that the cylindrical wall 22 of the raw tubing 20 is uniformly, preferably solely, of polymer material, having no heat conductive particles within it. As a result, the heat conductive particles 34 of the internal wall 32 could be said to be separated from the external surface 40 of the raw tubing 20 and, as a consequence, of the formed balloon.

Figure 4:
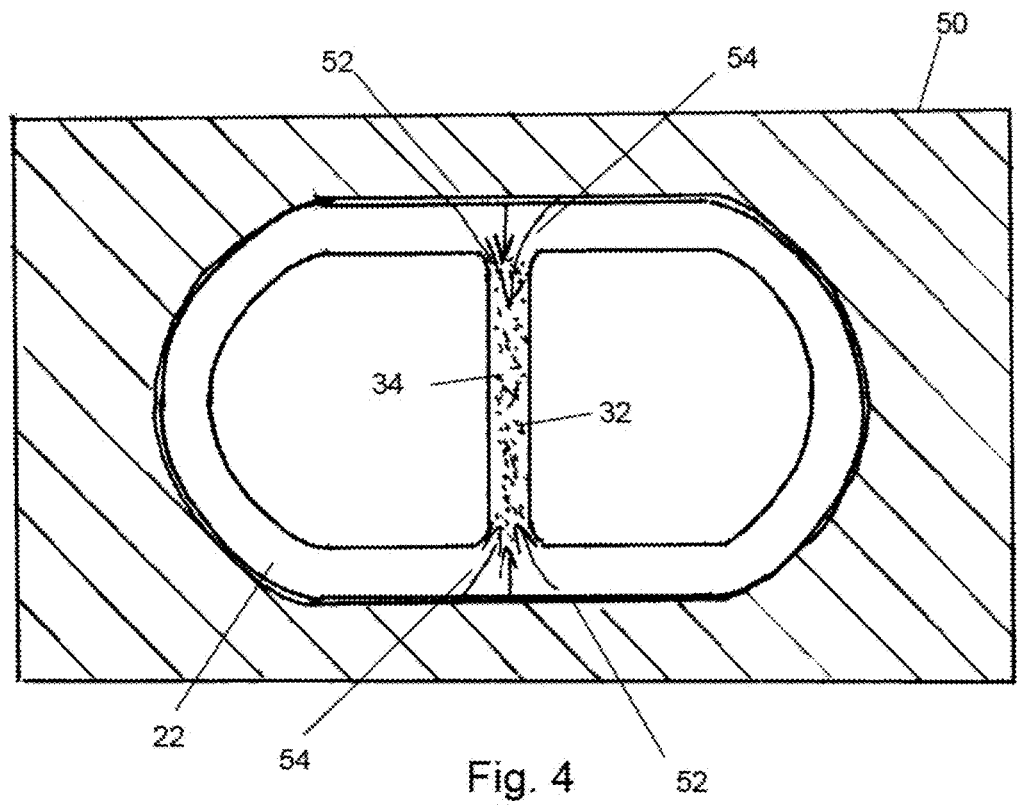
FIG. 4 is a schematic cross-sectional view of a medical balloon according to the teachings herein disposed in a balloon formation mold.

Referring now to FIG. 4, this shows in schematic form a transverse cross-sectional view of a mold chamber 50 used for forming a balloon from the raw tubing 10, 20 as taught herein. The mold 50 includes a mold chamber typically of heat conductive material which in practice is heated during the formation of the balloon. As a result, the internal surfaces 52 of the mold 50 become hot, for the purpose of imparting heat to the wall 22 of the raw tubing 20, which forms the balloon wall. This heat causes the polymer material of the wall 22 of the raw tubing to soften, enabling it to stretch when inflation fluid is pumped into the lumens 34, 36 of the raw tubing 20. As is known in the art, in practice, one end of the raw tubing 20 fitted within the mold 50 is sealed, while the other end is attached to a source of inflation fluid, such that inflation fluid will apply pressure from inside the raw tubing to cause it to inflate. It will be appreciated that the raw tubing 20 will typically be spaced from the internal surfaces 52 of the mold 50 at the start of the blowing operation and that the gap between the wall 22 and the internal surfaces 52 of the mold 50 will be heated by the heat from the mold 50, thereby to transfer heat to the walls 22 of the raw tubing 20 in order to cause this to soften.

With reference specifically to FIG. 4, the internal wall 32 of the raw tubing 20 is disposed within the outer wall 22. As a result of the poor thermal conductivity of the material of the outer tubing 24, the material of the internal wall 32 would not normally be heated to the same extent as the material of the wall 22. With an internal wall 32 made solely of a polymer material, this would not be sufficiently heated from heat from the mold 50 and consequentially will not soften or stretch. This can result in rupture of the structure (by separation of the internal wall from the external wall 22 or by tearing of the internal wall 22 or a combination of the two). Similarly, failure to heat and soften the internal wall 32 will cause it to retain its original dimensions and typically cause it to remain relatively thick, resulting in loss of flexibility of the formed balloon.

The provision of the heat conductive particles 34 within the internal wall 32 enables heat from the mold surfaces 52 to conduct through the particles 34 into the polymer material of the internal wall 32, as depicted by the arrows 54 in FIG. 4. The heat conductive particles 34, therefore, enable the polymer material of the remainder of the internal wall 32 to heat and soften, such as it stretches on expansion of the raw tubing, thereby maintaining structural integrity, as well as enabling the internal wall 32 to thin as it stretches. This makes the internal wall 32 more flexible, with a resultant optimisation of the flexibility of the formed balloon.

It should be appreciated that the shape of the internal surfaces 52 of the mold 50, which will determine the overall shape of the formed balloon, will not necessarily be as depicted in FIG. 4, which is schematic only. The mold 50 will have a shape consistent with that desired for the specific balloon to be formed, of which some examples are given below.

Figure 5:
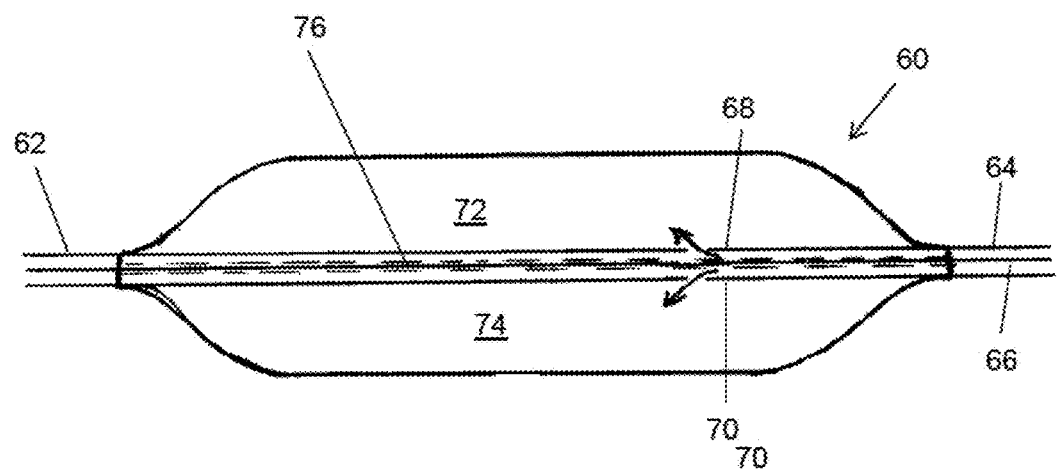
FIG. 5 is a side elevational view of a balloon catheter according to the teachings herein.
Figure 6:
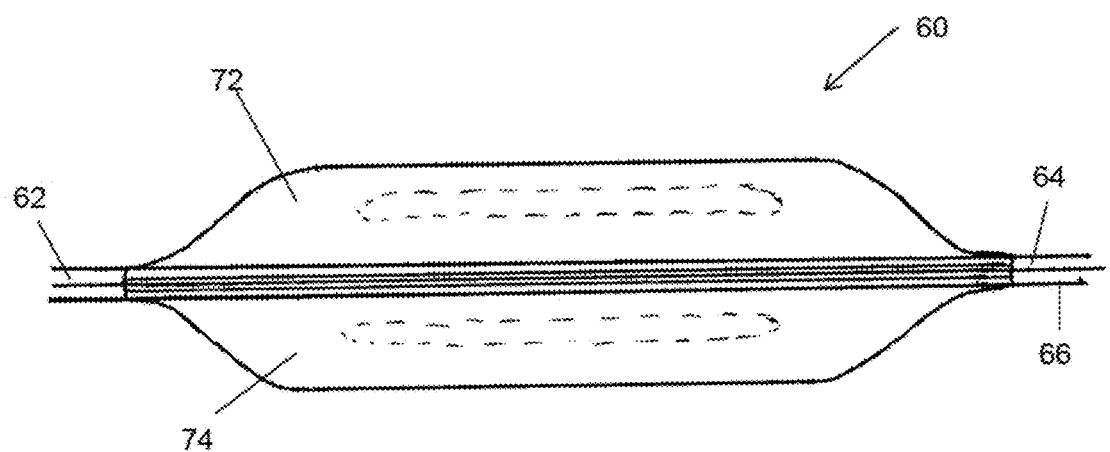
FIG. 6 is another side elevational view of the balloon catheter of FIG. 5

Referring now to FIGS. 5 and 6, these show two views of a balloon catheter 60 formed from the raw tubing 20 of FIG. 2 and by the method depicted in FIG. 4. With reference first to FIG. 5, the balloon 60 is fitted to a carrier catheter 62, of conventional form and which in this example includes first and second lumens 64, 66 therein which are separate from one another and which have respective ports 68, 70 open to respective chambers 72, 74 of the balloon 60. The chambers 72, 74 are separated from one another by the internal wall 76, which is shown in dotted outline in FIG. 5. The respective chambers 72, 74 of the balloon 60 can be inflated together or separately. The expanded profile of the balloon 60 can thus be determined by the relative state of inflation of each of the chambers 72, 74.

It is not necessary for the chambers 72, 74 to be separately inflatable and in some embodiments they could be inflated and deflated from a common lumen of the carry catheter 62.

Figure 7:
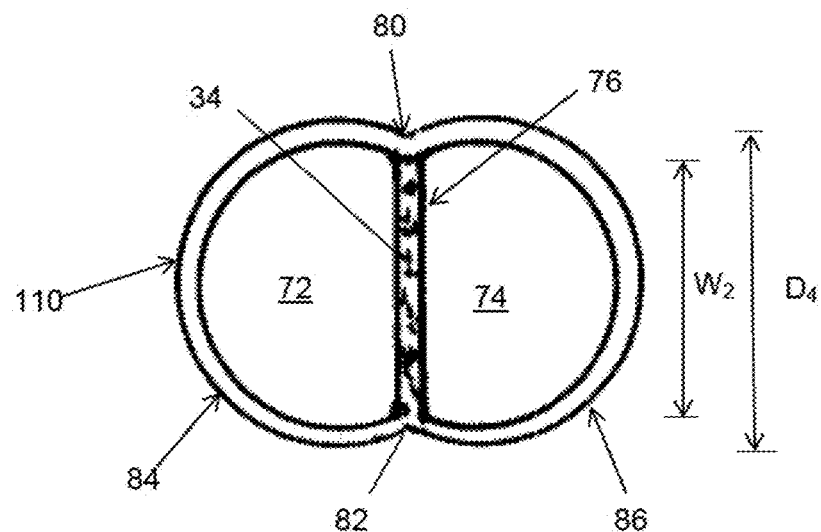
FIG. 7 is a transverse cross-sectional view of the medical balloon of FIGS. 5 and 6.

Reference is now made to FIG. 6 in conjunction with FIG. 7, the latter showing a transverse cross-sectional view of the inflated balloon 60 shown in FIG. 6. In this particular embodiment, the lateral extent of the balloon material forming each chamber 72, 74 is such that when the balloon is expanded, that is inflated, the two halves of the balloon expand to a diameter $D_4$ which is greater than the width $W_2$ of the internal wall 76, so as to create two depressions 80, 82 extending along the length of the balloon 60. The walls of the balloon 60 form what could be described as lobes either side of the internal wall 76. These depressions 80, 82 are useful in protecting parts of a patient's vessel or passageway which it is desired to protect from the inflation pressure of the balloon. A skilled person will appreciate that the depth of the depressions 80, 82 can be altered by altering the lateral extent (dimension) of the balloon wall forming each of the lobes 84, 86 of the inflated balloon 60. More balloon wall material for the lobes 84, 86 will result in deeper depressions 80, 82, whereas less material will result in the depressions being more shallow. In the case of a balloon made of conformable material, a similar effect can be achieved by changing the inflation pressure of the balloon.

Figure 8:
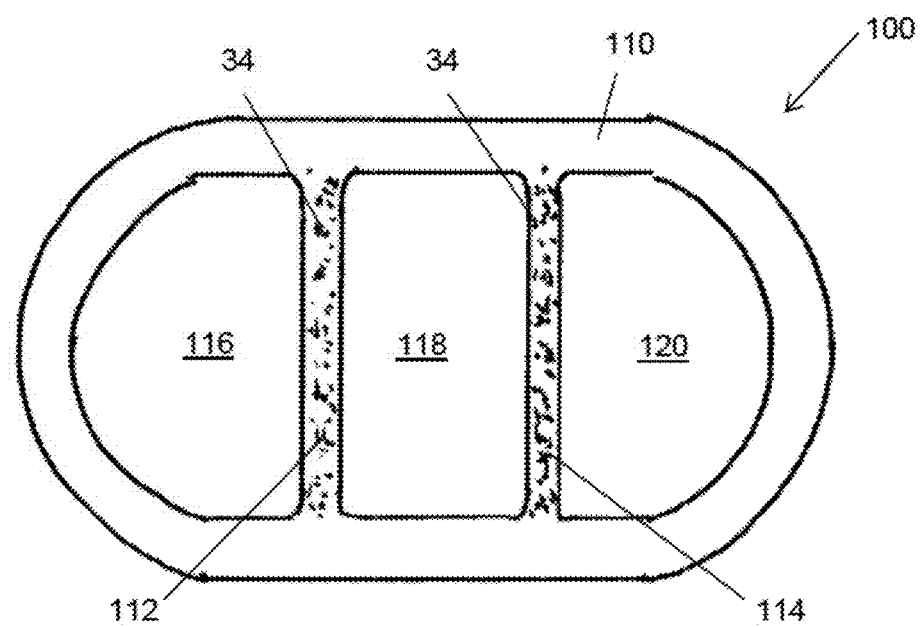
FIG. 8 is a transverse cross-sectional view of another embodiment of raw tubing for making a medical balloon.

FIG. 8 shows in schematic form a transverse cross-sectional view of an example of raw tubing 100 having an outer peripheral wall 110 and first and second internal walls 112, 114, extending throughout the length of the cylindrical portion 110, which form three internal chambers 116-120 within the raw tubing 100. Each of the internal walls 112, 114 has heat conductive particles 34 embedded therewithin and have the same characteristics as described above.

Figure 9:
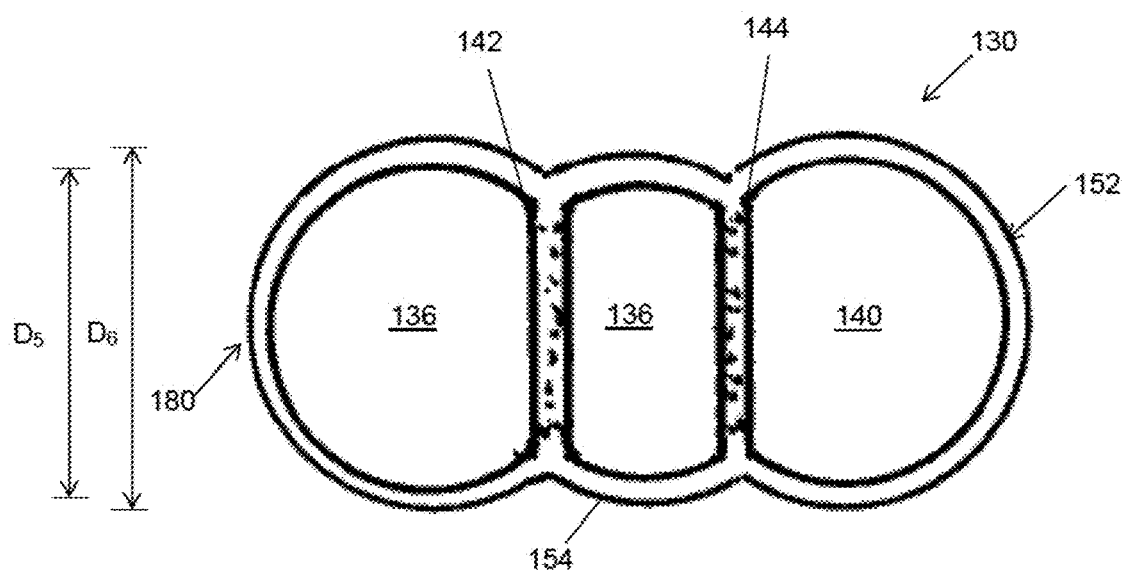
FIG. 9 is a transverse cross-sectional view of a medical balloon in inflated condition formed from the raw tubing of FIG. 8.

With reference to FIG. 9, this shows a transverse cross-sectional view of a balloon 130 formed from the raw tubing 100, in an expanded condition. The balloon has three internal chambers 136, 138, 140 each formed from a respected one of the chambers 116-120 of the raw tubing. The inflated balloon 130 shown in FIG. 9 has two lobes 150, 152 either side of a central portion 154 which may, as desired, have a smaller expanded depth $D_5$ compared to the depth $D_6$ of the lobes 150, 152. The skilled person will appreciate from the teachings herein that the relative dimensions of the three parts of the medical balloon 130 can be adjusted in the manner indicated above.

The balloon 130 can be fitted to a carrier catheter similar to that depicted in FIGS. 5 and 6, the catheter having one or more lumens with one or more ports extending into the chambers 136-140. The carry catheter may include separate lumens in order to inflate the chambers 136-140 independently of one another, and in other embodiments may have a common lumen to two or three of the chambers 136-140 so that these may be inflated together.

Figure 10:
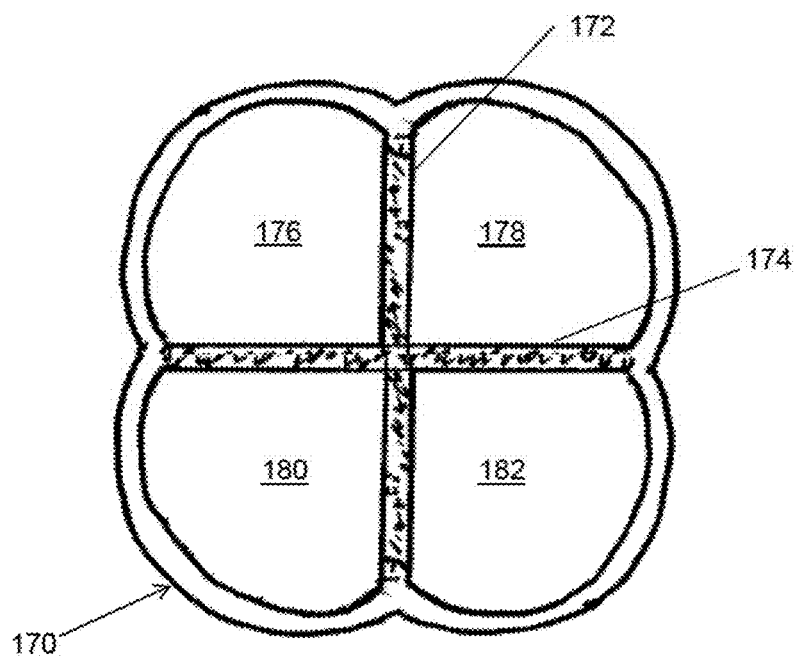
FIG. 10 is a transverse cross-sectional view of another embodiment medical balloon in inflated condition and having four internal chambers.

Another embodiment is shown in FIG. 10, which is a transverse cross-sectional view of a medical balloon 170 in an expanded state. The balloon 170 includes two internal walls 172, 174 which, as with the previous embodiments extend for the length of the balloon 170 and which in this embodiment cross one another to form four separate chambers 176-182. In the example of FIG. 10, the chambers 176-182 are of equal size, although other embodiments may have chambers of different sizes.

The raw tubing of all the embodiments disclosed herein can be formed by co-extrusion of the different parts.

The preferred embodiments, as described above, all seal the conductive particles 34 within the perimeter of the balloon, such that the heat conductive particles are not exposed to the patient's body.

It will be appreciated that the relative thicknesses $T_2$, $T_1$ of the internal wall or walls and of the outer wall of the balloon may vary from the examples given above. It is advantageous for the walls to be as thin as possible in order to increase the flexibility of the balloon and to reduce its footprint when the balloon is deflated, which enhance the trackability of the balloon through a patient's vasculature. The internal wall $T_2$ may be of the same thickness, thicker or thinner than the peripheral wall $T_1$ of the balloon.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1517831.2, from which this application claims priority, and in the abstract accompanying this application, are incorporated herein by reference.

The invention claimed is:

1. A medical balloon assembly including a balloon having a body portion, the body portion being formed of a balloon wall providing an expandable volume within the balloon, the expandable volume being divided into a plurality of chambers by a least one internal wall extending between opposing sides of the balloon wall, the balloon wall and internal wall or walls being formed from a flexible polymer material, the polymer material of the internal wall having heat conductive particles embedded therein such that the internal wall includes at least 50% by weight of heat conductive particles.

2. An assembly according to claim 1, wherein the balloon wall has exterior and interior surfaces and a wall thickness between the exterior and interior surfaces, the internal wall or walls extending to the interior surface of the balloon body portion and not to the exterior surface.

3. An assembly according to claim 1, wherein the balloon body portion is substantially free of the heat conductive particles of the internal wall or walls.

4. An assembly according to claim 1, wherein the heat conductive particles are of or include a metal or metal alloy.

5. An assembly according to claim 1, wherein the body portion includes a major portion, preferably of generally cylindrical form, and the internal wall extends throughout the length of the major portion and is attached to or otherwise integral with opposing sides of the major portion, preferably throughout the length of the major portion.

6. An assembly according to claim 1, wherein the heat conductive particles are of or include a radiopaque material.

7. An assembly according to claim 1, wherein the heat conductive particles are of or include at least one of: tungsten, boron, gold, silver, platinum, palladium and copper.

8. The assembly according to claim 1,
wherein the density of heat conductive particles in the at least one internal wall is around 2 g/cc.

9. An assembly according to claim 1, wherein the heat conductive particles are one of substantially round or elongate shape, wherein the heat conductive particles optionally have a rounded oblong shape.

10. An assembly according to claim 1, wherein the heat conductive particles are substantially evenly distributed throughout the internal wall or walls.

11. An assembly according to claim 1, wherein the balloon wall and the internal wall or walls are made from the same polymer material; and/or wherein the balloon wall and the internal wall or walls are made from a polyamide, optionally nylon 12.

12. An assembly according to claim 1, wherein the body portion is generally circular or generally non-circular, optionally generally oval, in transverse cross-section.

13. An assembly according to claim 1, wherein the at least one internal wall generates an external channel or depression in an exterior surface of the balloon when the balloon is inflated and/or divides the balloon into fluidically separate chambers.

14. The assembly of claim 1, wherein the heat conductive particles have an average particle size of 0.50 to 2.0 micrometers.

15. An assembly according to claim 1, including a plurality of internal walls.

16. An assembly according to claim 15, wherein the or at least two of said internal walls are disposed substantially parallel to one another or to cross one another.

17. The assembly of claim 1, wherein the heat conductive particles have a thermal conductivity of at least about 50 times greater than a thermal conductivity of the material of the inner wall.

18. The assembly of claim 17, wherein the heat conductive particles have a thermal conductivity of at least about 500 times greater than a thermal conductivity of the material of the inner wall.

19. The assembly of claim 1, wherein the heat conductive particles have a thermal conductivity of at least 20 W/mK.

20. The assembly of claim 19, wherein the heat conductive particles have a thermal conductivity of at least 150 W/mK.

* * * * *